US010722732B2

(12) United States Patent
Hsu et al.

(10) Patent No.: US 10,722,732 B2
(45) Date of Patent: *Jul. 28, 2020

(54) MULTI LEVEL MULTILEAF COLLIMATOR LEAF TIP SHAPE EFFECTS AND PENUMBRA OPTIMIZATION

(71) Applicants: Varian Medical Systems, Inc., Palo Alto, CA (US); Varian Medical Systems International AG, Zug (CH)

(72) Inventors: HsinLu Hsu, Sunnyvale, CA (US); Ross Hannibal, Saratoga, CA (US); Steven W. Prince, San Francisco, CA (US); Janne Nord, Espoo (FI)

(73) Assignee: Varian Medical Systems, Inc., Palo Alto, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 15/844,158

(22) Filed: Dec. 15, 2017

(65) Prior Publication Data
US 2018/0104511 A1    Apr. 19, 2018

Related U.S. Application Data

(63) Continuation of application No. 14/225,411, filed on Mar. 25, 2014.

(51) Int. Cl.
*A61N 5/10* (2006.01)

(52) U.S. Cl.
CPC .................................. *A61N 5/1045* (2013.01)

(58) Field of Classification Search
None
See application file for complete search history.

(56) References Cited

U.S. PATENT DOCUMENTS 9,931,521 B2 *   4/2018  Hsu .................... A61N 5/1045
2012/0043482 A1 * 2/2012  Prince ................. G21K 1/046
                                                   250/505.1

* cited by examiner

*Primary Examiner* — Hoon K Song
(74) *Attorney, Agent, or Firm* — Varian IP Legal

(57) ABSTRACT

A multi level multileaf collimator employs leaves with leaf tips having a non-square shape in a beam's eye view to improve beam shaping effect and penumbra performance. The multi level multileaf collimator includes a first multileaf collimator in a first level comprising beam blocking leaves longitudinally movable in a first direction, and a second multileaf collimator in a second level comprising beam blocking leaves longitudinally movable in a second direction. The first direction may be generally parallel with the second direction and the leaves of the first multileaf collimator may laterally offset the leaves of the second multileaf collimator. The beam blocking leaves of the first multileaf collimator may comprise an end portion having a non-square shape in a beam's eye view.

15 Claims, 9 Drawing Sheets

—— UPPER LEVEL LEAVES
—— LOWER LEVEL LEAVES

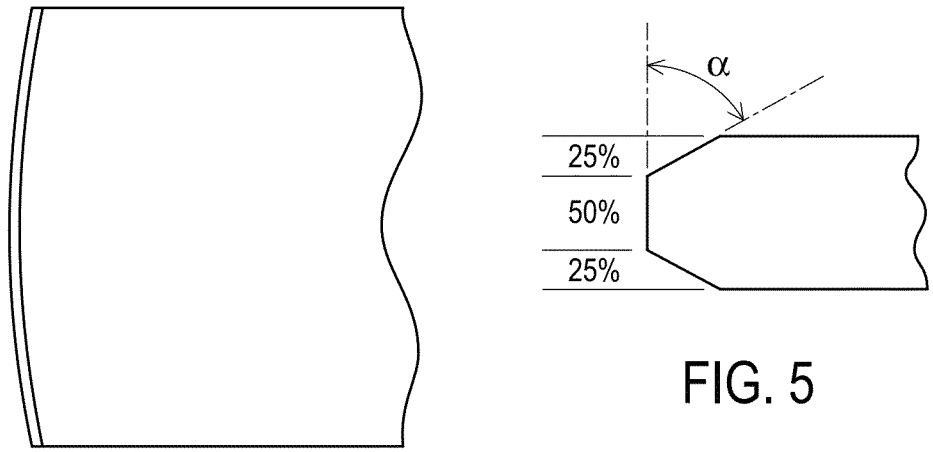
FIG. 4
FIG. 5
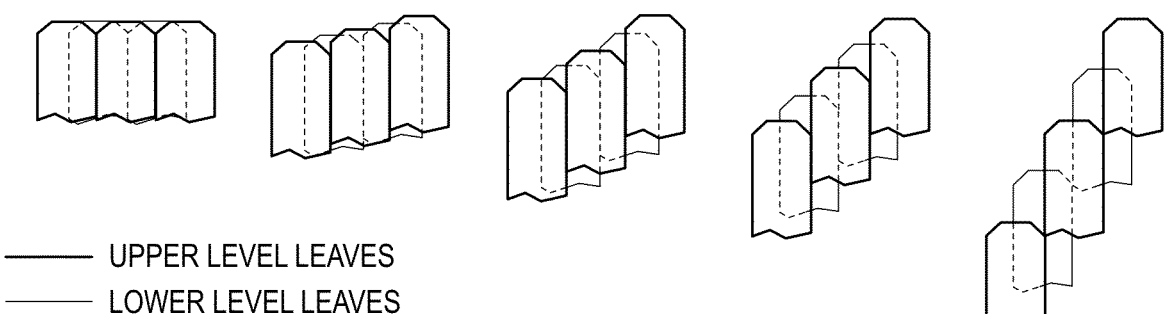
——— UPPER LEVEL LEAVES
——— LOWER LEVEL LEAVES
FIG. 6

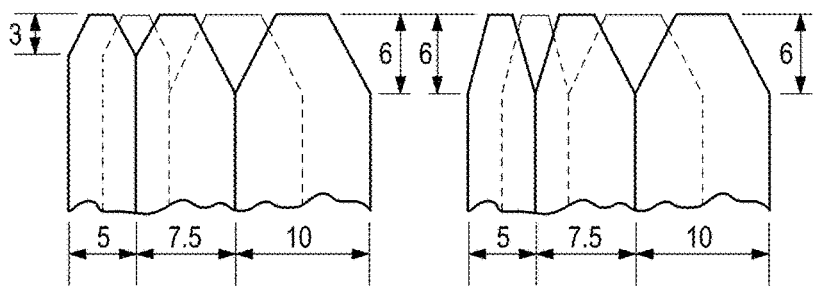
FIG. 9A — SAME ANGLE CHAMFERS
FIG. 9B — SAME LENGTH CHAMFERS
FIG. 9C — COMPOUND CHAMFERS
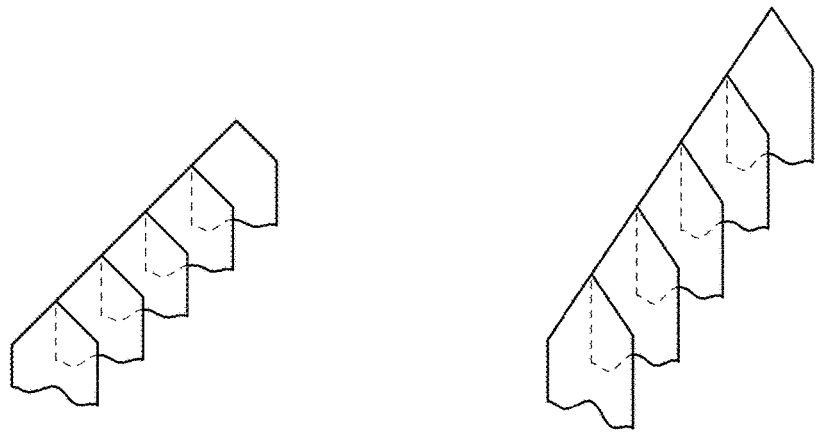
FIG. 10A
FIG. 10B

— UPPER LEVEL LEAVES
---- LOWER LEVEL LEAVES

— UPPER LEVEL LEAVES
---- LOWER LEVEL LEAVES

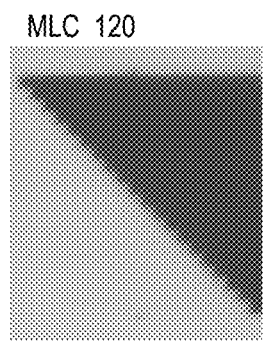
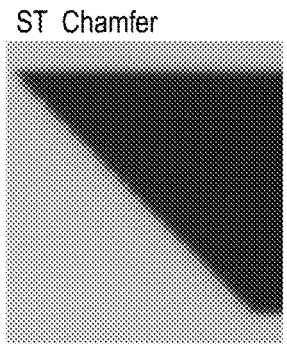
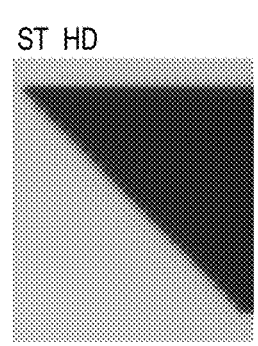
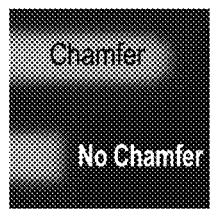
FIG. 17A  FIG. 17B  FIG. 17C  FIG. 17D
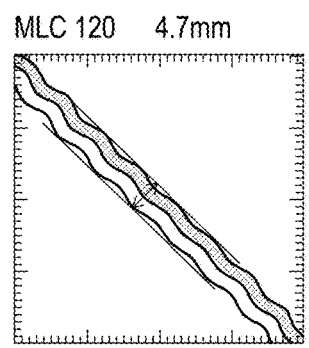
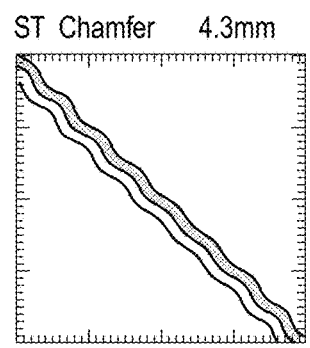
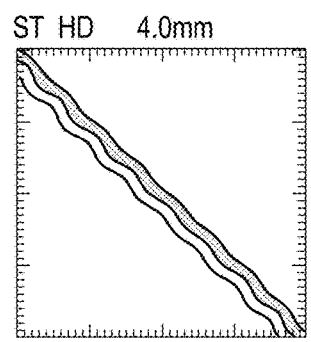
FIG. 18A  FIG. 18B  FIG. 18C

MULTI LEVEL MULTILEAF COLLIMATOR LEAF TIP SHAPE EFFECTS AND PENUMBRA OPTIMIZATION

This application is a continuation of U.S. application Ser. No. 14/225,411 filed Mar. 25, 2014, entitled "MULTI-LEVEL MULTILEAF COLLIMATOR LEAF TIP SHAPE EFFECTS AND PENUMBRA OPTIMIZATION," the disclosure of all of which is incorporated herein by reference in its entirety.

BACKGROUND

This disclosure relates generally to radiation apparatuses and methods, and in particular to multi level multileaf collimator (MLC) leaf tip effects and penumbra optimization using multi level MLCs.

Multileaf collimators are widely used in radiotherapy machines to support various treatments including intensity-modulated radiation therapy (IMRT) and volumetric modulated arc therapy (VMAT). Conventional multileaf collimators include a single level of a plurality of beam blocking leaves arranged in two opposing banks or arrays. Each leaf in a bank is longitudinally movable relative to a leaf in the opposing bank. In operation, each of the individual leaves is positioned to block a portion of a radiation beam passing through the volume occupied by the leaf. The combined positioning of all leaves defines one or more apertures through which the unblocked radiation beam passes, and the aperture(s) define(s) the shape of the radiation beam directed to a treatment field in an isocenter plane.

It would be desirable to provide MLCs that can shape beams with high resolution so that the shaped beam conforms to a target volume as close as possible. Conventional single level MLCs have been designed to provide higher beam shaping resolution by making the beam blocking leaves thin. However, reducing the width of leaves to improve MLC resolution has limitations and imposes challenges to MLC construction and operation. For MLCs using screw leaf drive systems for example, long slender drive screws may be susceptible to column buckling in a way that scales dramatically worse with smaller screw diameters. Motors with a smaller diameter may also be required.

Conventional single level MLCs employs square leaf tips in a beam's eye view. Therefore, even with width resolution of 5-10 mm, conventional single level MLCs can only create a "stairstep" approximation of the desired treatment field.

Furthermore, conventional single level MLCs use single leaf tip design, which is generally optimized for penumbra performance for a small specific area in the treatment field but not for the other areas or large fields. Further, while single leaf tip design may provide optimal penumbra performance on a specific field contour, it may perform less desirably on various other contours due to the finite resolution of the leaf width and leaf tip geometry.

SUMMARY

Embodiments of multi level MLCs with various leaf tip designs are described to improve the shaping of treatment field perimeters. Also described are methods of treatment panning and penumbra optimization of treatment fields using multi level MLCs. Other embodiments are described further herein.

BRIEF DESCRIPTION OF THE DRAWINGS

These and various other features and advantages will become better understood upon reading of the following detailed description in conjunction with the accompanying drawings and the appended claims provided below, where:

FIG. 4 is a side view of an exemplary chamfer leaf according to some embodiments of this disclosure;

FIG. 5 is a beam's eye view of the exemplary chamfer leaf shown in FIG. 4;

FIG. 6 schematically shows the shaping effects of chamfer leaves on a two level parallel MLC according some embodiments of this disclosure;

FIGS. 9A-9C schematically show various chamfer leaf designs for leaf transition in a multi level MLC according to some embodiments of this disclosure;

FIGS. 10A-10B schematically show exemplary chamfer leaf designs according to some embodiments of this disclosure;

FIGS. 17A-17D show images of field edges shaped by a conventional single level MLC and two level MLCs according to embodiments of this disclosure; and FIGS. 18A-18C show images of effective penumbra produced by a conventional single level MLC and two level MLCs according to embodiments of this disclosure.

DETAILED DESCRIPTION

Various embodiments of multi level MLCs are described. It is to be understood that the invention is not limited to the particular embodiments described as such may, of course, vary. An aspect described in conjunction with a particular embodiment is not necessarily limited to that embodiment and can be practiced in any other embodiments. For instance, while various embodiments are described in connection with two level multileaf collimators, it will be appreciated that the disclosure can also be practiced in multileaf collimators in more than two levels. Further, in the following description, numerous specific details such as examples of specific components, dimensions, processes, etc. may be set forth in order to provide a thorough understanding of the disclosure. It will be apparent, however, to one of ordinary skill in the art that these specific details need not be employed to practice embodiments of the disclosure. In other instances, well known components or steps may not be described in detail in order to avoid unnecessarily obscuring the embodiments of the disclosure.

Various relative terms such as "upper," "above," "top," "over," "on," "below," "under," "bottom," "higher," "lower" or similar terms may be used herein for convenience in describing relative positions, directions, or spatial relationships in conjunction with the drawings. For example, the terms "upper level" or "lower level" may be used for ease of describing some embodiments when a radiation source is on the top of an isocenter and a multi level MLC is positioned therebetween. The use of the relative terms should not be construed as to imply a necessary positioning, orientation, or direction of the structures or portions thereof in manufacturing or use, and to limit the scope of the invention. As used in the description and appended claims, the singular forms of "a," "an," and "the" include plural references unless the context clearly dictates otherwise. The term "or" refers to a nonexclusive "or" unless the context clearly dictates otherwise.

Exemplary embodiments will now be described with reference to the figures. It should be noted that some figures are not necessarily drawn to scale. The figures are only intended to facilitate the description of specific embodiments, and are not intended as an exhaustive description or as a limitation on the scope of the disclosure.

Figure 1:
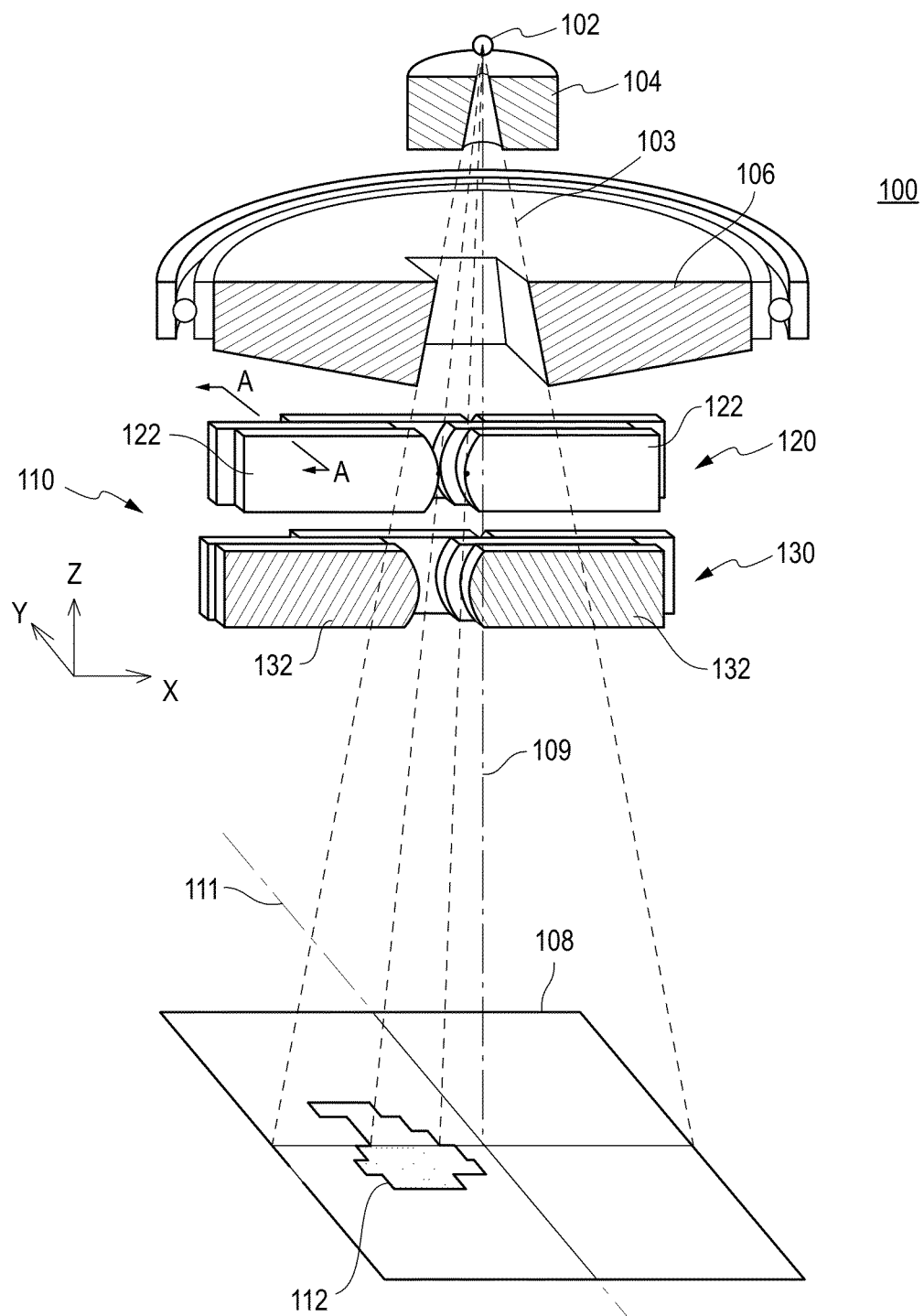
FIG. 1 schematically illustrates a radiation system that includes a multi level MLC in accordance with some embodiments of this disclosure.

FIG. 1 is a simplified illustration of a radiation system 100 that includes an exemplary multi level MLC according to some embodiments of this disclosure. The radiation system 100 may include a radiation source 102 configured to produce beams 103 such as of photons, electrons, protons, or other types of radiation. By way of example, in X-ray radiotherapy, the radiation source 102 may be configured to produce X-ray radiation. The radiation system 100 may include various beam shaping components such as a primary collimator 104 and optionally a secondary collimator 106 to generally limit the extent of the beam 103 as it travels away from the radiation source 102 toward an isocenter plane 108. A multi level MLC 110, which will be described in greater detail below, may be disposed between the radiation source 102 and the isocenter plane 108 to further shape the beam, as indicated by the shaped field 112 in the isocenter plane 108. The multi level MLC 110 and optionally the secondary collimator 106 may rotate about an axis 109 through the source 102. The radiation source 102, primary collimator 104, secondary collimator 106, and the multi level MLC 110 may be enclosed in or attached to a structure such as a gantry (not shown), which may rotate about an axis such as a horizontal axis 111. Thus, the radiation system 100 may deliver treatment beams to a target in the isocenter plane 108 from various angles, and the shape and/or intensity of the beams can be dynamically adjusted by the multi level MLC 110 as the beam angle is swept or stepped around the target.

The multi level MLC 110 may include a first MLC 120 proximal to the source 102 (or in a first level) and a second MLC 130 distal to the source 102 (or in a second level). As used herein, the term "MLC" or "multileaf collimator" refers to a collection of a plurality of beam blocking leaves each of which can be independently moved in and out of a beam to modify one or more parameters of the beam such as the beam shape, size, energy, or intensity etc. The beam blocking leaves of an MLC may be arranged in pairs and disposed in opposing banks. The beam blocking leaves of each pair may be longitudinally movable relative to each other.

As shown in FIG. 1, the first and second MLCs 120, 130 may be arranged stacked and parallel. As used herein, the term "parallel" refer to the moving direction of the leaves of the first and second MLCs 120, 130. In each of the first and second MLCs 120, 130, a plurality of beam blocking leaves 122, 132 may be arranged in two banks, forming a plurality of pairs of opposing leaves. Leaves 122 of each pair of the first MLC 120 in the first level can be longitudinally movable in a first direction. Leaves 132 of each pair of the second MLC 130 in the second level can be longitudinally movable in a second direction. The first direction and the second direction may be substantially parallel. Alternatively, the first and second MLCs are arranged such that the first direction and the second direction may be non-parallel.

The leaves 122, 132 of the multi level MLC 110 may be supported by a support body such as a frame, box, carriage or other support structures (not shown in FIG. 1). By way of example, all leaves of the first and second MLCs 120, 122 may be carried by a single carriage (unicarriage). The single carriage may be further moved or translated in addition to the individual leaf travel. Alternatively, leaves 122 of the first MLC 120 and leaves 132 of the second MLC 130 may be separately supported or carried by different carriages respectively. In some embodiments, all leaves of the first and second MLCs 120, 130 in a same bank may be carried by a carriage and all leaves of the first and second MLCs 120, 130 in the opposing bank may be carried by another carriage. The two carriages may be independently moved in addition to the individual leaf travel. In some embodiments, the multi level MLC 110 of the disclosure does not require a movable carriage or carriages (carriageless).

Figure 2:
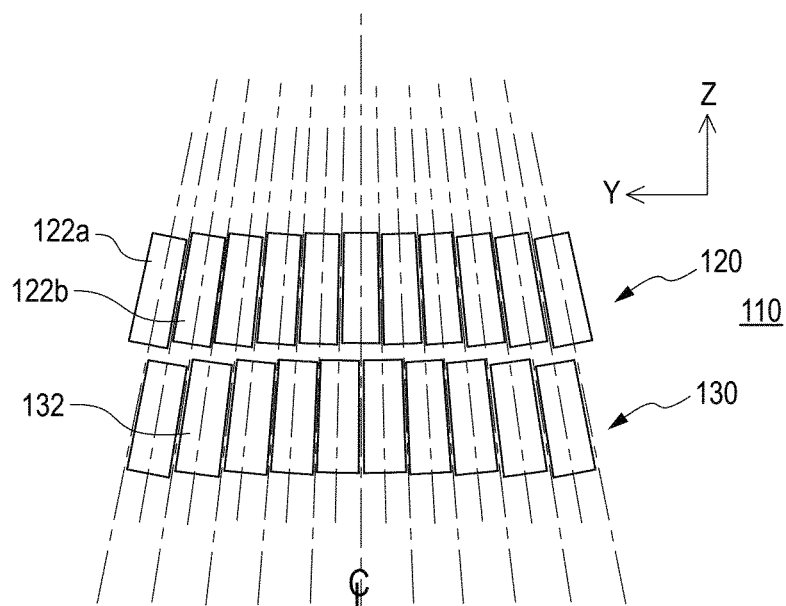
FIG. 2 is a cross-sectional view of a portion of the multi level MLC shown in FIG. 1, taken along line A-A.

The first and second MLCs 120, 130 may be disposed such that the leaves 122 of the first MLC 120 may laterally offset the leaves 132 of the second MLC 130 as viewed from the source 102. FIG. 2 is a cross-sectional view of a portion of the multi level MLC 110 taken along line A-A in FIG. 1, showing an offset arrangement of the leaves of the multi level MLC 110. As shown, each leaf of the first MLC 120 in the first level may offset from a leaf of the second MLC 130 in the second level as viewed from the source. By way of example, a leaf of the first MLC 120 may offset from a leaf of the second MLC 130 by substantially half a leaf. Alternatively, a gap between two adjacent leaves of the first MLC 120 in the first level (e.g. the gap between leaves 122a, 122b of the first MLC 120) may be positioned substantially at the middle of a leaf of the second MLC 130 (e.g. leaf 132 of the second MLC 130). The offset arrangement of leaves in different levels provides for leaf projections that are also offset at the isocenter plane. Therefore, the leaf offset arrangement may provide for substantially an equivalent of doubling MLC definition, or improving the resolution to half as compared to the definition of a single level MLC with leaves of the same physical width. In some embodiments, three or more MLCs may be arranged in three or more levels such that each leaf at a level may offset e.g. by ⅓ or 1/n of a leaf width as projected at the isocenter plane where n is the number of the MLCs. U.S. application Ser. No. 12/861,368 filed Aug. 23, 2010 and entitled "Multi Level Multileaf Collimators" describes various embodiments of multi level MLCs. U.S. application Ser. No. 12/861,368 is incorporated herein by reference in its entirety.

The individual leaves 122, 132 may have various leaf end or tip configurations. To facilitate description of the multi level MLC 110 of this disclosure, various terms such as "length," "width," "height," "side," and "end," "tip" may be used. As used herein, the "length" of a leaf refers to the leaf dimension that is parallel to the leaf longitudinal moving direction. The "height" of a leaf refers to the dimension of the leaf along the beam direction. The "width" of a leaf refers to the dimension of the leaf that is traverse the leaf moving direction and the direction of the radiation beam. The "side surface" of a leaf refers to the surface of the leaf in contact with or adjacent to neighboring leaves. The "end surface" of a leaf refers to the surface of the leaf inserted into the field and generally transverse to the leaf longitudinal moving direction. The "end portion" of a leaf refers to the portion of the leaf including the end surface. In this disclosure, the term "leaf tip" may be used interchangeably with the term "leaf end portion" or "end portion of a leaf." In description of various leaf tip configurations, the term "beam's eye view" may be used to describe a view observed from the radiation source. The term "side view" may be used to describe a view observed from a side surface of the leaf.

Returning to FIG. 1, the individual leaves 122, 132 may have various leaf tip configurations. For example, the end surface of a leaf may be flat. Thus, in both a side view and a beam's eye view, a leaf tip with a flat end surface may be shown as having a straight line orthogonal to the leaf longitudinal moving direction and two right angles at each side of the straight line.

The end surface of a leaf tip may be curved. The curved end surface may be continuous and transverse the entire height of the leaf. Thus, in a side view, an end portion of a leaf with a curved end surface may be shown as having a curved line with a radius and two parallel lines on either side of the curved line. In a beam's eye, an end portion of a leaf with a curved end surface may be shown as having a straight line orthogonal to the leaf longitudinal moving direction and two right angles on each side of the straight line. In the Detail Description and appended Claims, the term "square shape" may be used to describe a leaf tip configuration which, in a beam's eye view, has a straight line orthogonal to the leaf longitudinal moving direction and two right angles on each side of the straight line. The term "non-square shape" may be used to describe any leaf tip configuration which, in a beam's eye view, does not have a square shape. The non-square shape in a beam's eye view may include a curved or elliptic shape and a shape of a chamfer leaf which may include a combination of a straight portion and a beveled portion on each side of the straight portion as will be described in greater detail below.

Figure 3:
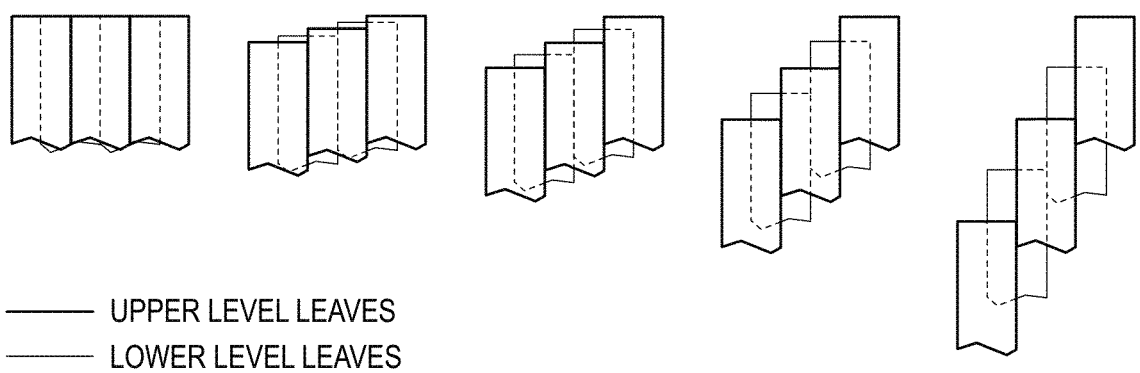
FIG. 3 schematically shows the shaping effects of square leaf tips on a two level parallel MLC.

FIG. 3 schematically shows the shaping effect of a two level parallel MLC comprising leaves having leaf tips with a square shape in a beam's eye view. As shown in FIG. 3, the square leaf tips on a two level MLC may provide conformal shaping for a field with an edge or a contour that is substantially orthogonal to the leaf longitudinal travel direction. However, to shape a field with an increasing slope or increasing angle with respect to the direction orthogonal to the leaf travel direction, the square leaf tips (in a beam's eye view) show poor stair-step conformance to the field edges.

In various embodiments of this disclosure, the end surface of a leaf may include a combination of a curved surface and a beveled or flat surface on each side of the curved surface. Both the curved surface and the beveled surfaces may be generally transverse the entire height of the leaf. The term "chamfer leaf" may be used herein to refer to a leaf which includes a combination of a curved end surface generally transverse the entire height of the leaf and beveled end surfaces on each side of the curved end surface and generally transverse the entire height of the leaf.

FIG. 4 is a side view of an exemplary chamfer leaf tip according to embodiments of this disclosure. FIG. 5 is a beam's eye view of the exemplary chamfer leaf tip shown in FIG. 4. In a side view of FIG. 4, the end portion of a chamfer leaf may be shown as having a curve with a radius and two parallel lines. In a beam's eye view of FIG. 5, the end portion of a chamfer leaf may be shown as having a straight middle portion orthogonal to the leaf longitudinal moving direction and beveled portions on each side of the straight middle portion. The term "chamfer angle" (alpha) may used herein to refer to the acute angle between the beveled line and the straight line in a beam's eye view. By way of example, the straight middle portion of a chamfer leaf tip in a beam's eye view may be approximately 50% of the leaf width, and the remaining 25% on each side of the middle portion can be shaped in any different chamfer angles optimized for various different field slopes. In general, the chamfer angles may range from 5-95 degrees, or from 10-90 degrees, or from 20-80 degrees, or from 40-60 degrees. In a specific example, the chamfer angle (alpha) may be about 45 degree. In a further specific example, the chamfer angle may be about 60 degree. In certain embodiment, a chamfer leaf may have a straight middle portion about 50% of the leaf width, with the remaining 25% on each side being beveled with a chamfer angle of about 60 degree.

FIG. 6 schematically shows the shaping effect of a two level parallel MLC comprising chamfer leaves. The chamfer leaves comprise an end portion which has, in a beam's eye view, a straight middle portion orthogonal to the leaf longitudinal moving direction and beveled portions on each side of the straight middle portion. As shown in FIG. 6, a two level MLC comprising chamfer leaves may provide substantially conformal shaping for a field with an edge substantially orthogonal to the leaf longitudinal travel direction. Therefore, for shaping a field edge generally orthogonal to the leaf travel direction, chamfer leaves may provide a shaping effect substantially as conformal as leaves with leaf tips having a square shape in a beam's eye view. Further, to shape a field with an increasing slope or increasing angle with respect to the leaf end surface in a beam's eye view, the chamfer leaves provide better shaping conformance than that provided by leaves with leaf tips having a square shape in a beam's eye view.

Figures 7A, 7B:
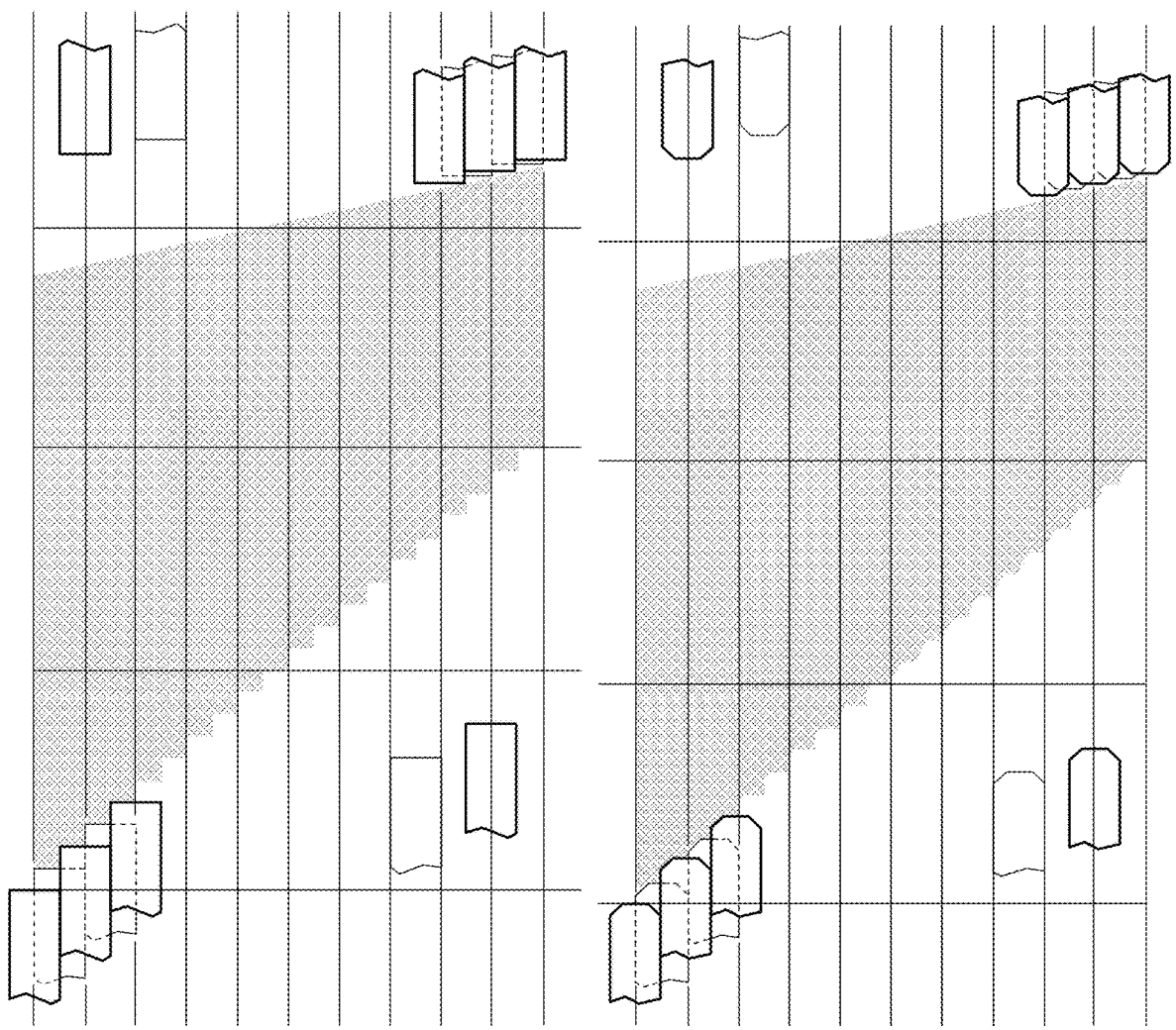
FIGS. 7A and 7B shows images of fields shaped by square leaf tips and chamfer leaf tips according to some embodiments of this disclosure.

FIG. 7 provides further comparison on shaping fields having a 45 degree edge or contour. The gray area in FIG. 7A is a field shaped by a two-level MLC comprising leaves with leaf tips having a square shape in a beam's eye view. The gray area in FIG. 7B is a field shaped by a two-level MLC comprising chamfer leaves. FIGS. 7A-7B show that the field edge shaped by chamfer leaves has significantly reduced undesired "scalloping" effect as compared with the field edge shaped by leaf tips having a square shape in a beam's eye view.

Figure 8:
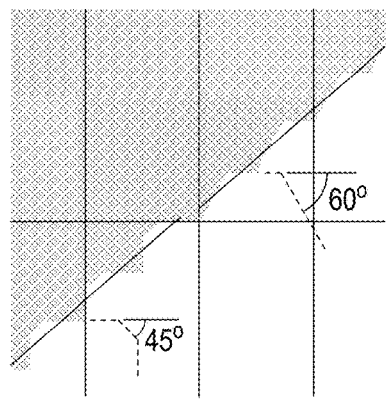
FIG. 8 is an enlarged view of a shaped field showing the shaping effects of chamfer leaf tips with different chamfer angles according to some embodiments of this disclosure.

FIG. 8 is an enlarged view of a shaped field showing the shaping effect of different chamfer leaf tips. FIG. 8 shows that to shape a 45 degree field edge, chamfer leaf tips with a steeper angle such as about 60 degree chamfer angle may make the underdosed and overdosed area both equal and most minimized, as compared to chamfer leaf tips with a 45 degree chamfer angle. Therefore, chamfer leaves may be further configured to have different chamfer angles to accommodate various field edges in applications.

In some embodiments, the length and the number of beveled portions on each side of the straight middle portion of a chamfer leaf may be varied to accommodate various applications. A multi level MLC of this disclosure may define a treatment field with variant width definitions at the isocenter plane. For example, a finer definition may be provided in the central portion of the treatment field where precision is more needed. This may reduce MLC cost and increase MLC reliability compared to an MLC with a greater number of leaves allowing fine definition throughout the entire treatment field. The transition of leaf width can be gradual. For example, the width of leaves at a level can be progressively increased with distance from the center of the treatment field. Each leaf at a level may have a physically different width dimension. Alternatively, each MLC level may include leaf sections so that the transition of leaf widths is discreet. The transition can be made by placing transition leaves at specific locations on both levels. The transition leaves insure that the gaps between leaves project at the desired spacing for the desired definition regions. FIGS. 9A-9C show that in conjunction with leaf width transition, the chamfer angles of the leaves can remain the same (FIG. 9A), or the length of the beveled portions of the leaves can remain the same (FIG. 9B). FIG. 9C shows that two or more beveled portions can be made on each side of the straight middle portion of a chamfer leaf (compound chamfer leaf).

In some specific embodiment, the end surface of a leaf may consist of two beveled or flat surfaces generally transverse the entire height of the leaf. This may be a special case of a chamfer leaf where the curved end surface is reduced to a one-dimensional curved line. Thus, in a beam's eye view, the end portion of such leaf may be shown as having two beveled lines forming an acute, right, or obtuse angle. In a side view, the leaf end portion of such leaf may be shown as having a curved line and two parallel lines on each side of the curved line. The term "50-50 chamfer leaf" or "pointed chamfer leaf" may be used to refer to a leaf having an end portion which, in a beam's eye view, has two beveled portions forming an acute, right, or obtuse angle. FIGS. 10A and 10B show exemplary 50-50 chamfer leaves and their shaping effects for various field edges.

In some specific embodiment, the end surface of a leaf may be curved and/or rounded. The curved/rounded end surface may be machined such that the end surface has a curvature both transverse the entire height of the leaf and the entire width of the leaf. Thus, in both a side view and a beam's eye view, the end portion of such leaf may be shown as having a curved line with a radius. In some embodiment, the end surface of a leaf may be configured such that in a beam's eye view, the end portion of the leaf has an elliptic shape. Other designs of the end surface are possible. For example, the end surface may have a curvature transverse the entire height of the leaf but with no curvature along the width. Alternatively, the end surface may have a curvature transverse the entire width of the leaf but with no curvature along the height.

Figure 11:
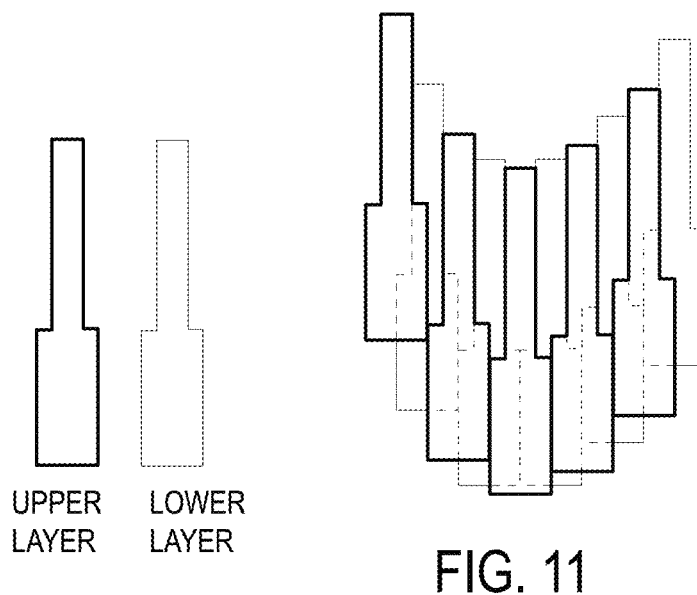
FIG. 11 schematically shows an exemplary symmetrical finger leaf design and the combined shaping effects according to some embodiments of this disclosure.
Figure 12:
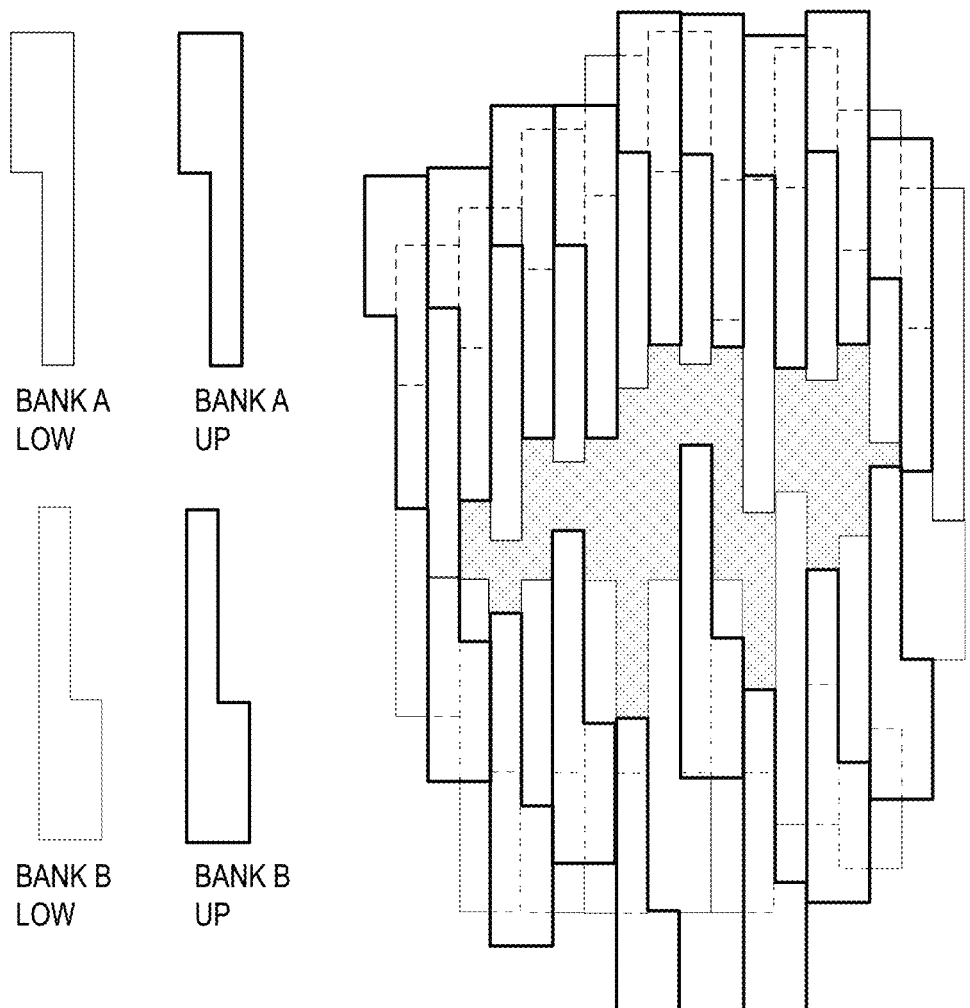
FIG. 12 schematically shows exemplary asymmetrical finger leaf designs and the combined shaping effects according to some embodiments of this disclosure.

In some embodiment, the disclosure provides a multi level MLC comprising a first MLC in a first level comprising first beam blocking leaves longitudinally movable in a first direction, and a second MLC in a second level comprising beam blocking leaves longitudinally movable in a second direction generally parallel with the first direction. The first beam blocking leaves of the first MLC comprise finger leaves, and the second beam blocking leaves of the second MLC comprise finger leaves. As used herein, the term "finger leaf" refers to a leaf having an elongate end portion or tip with a reduced or constant width transverse the entire height of the leaf. A finger leaf may be symmetric or asymmetric. In a symmetric finger leaf, the elongate end portion with a reduced width extends from the middle of the leaf width. In an asymmetric finger leaf, the elongate end portion with a reduced width extends from a side of the leaf width. FIG. 11 schematically shows exemplary symmetrical finger leaves and the combined shaping effects of a two level MLC comprising the symmetrical finger leaves. FIG. 12 schematically shows exemplary asymmetrical finger leaves and the combined shaping effects of a two level MLC comprising the asymmetrical finger leaves.

Figure 13:
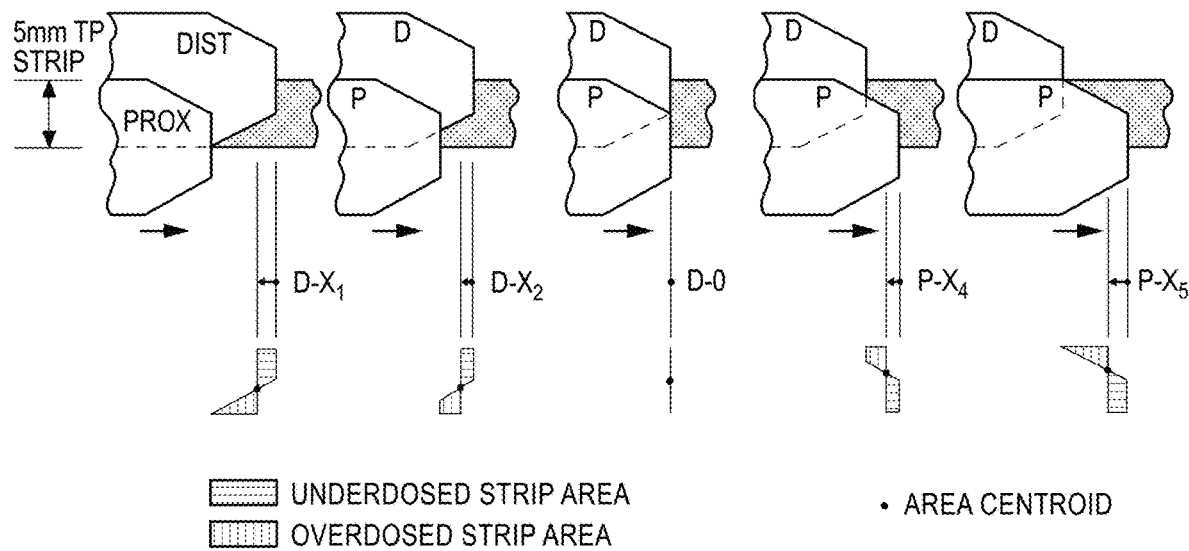
FIG. 13 schematically illustrates an exemplary treatment planning method according to some embodiments of this disclosure.

The variations of leaf tip shape may present problems for treatment planning (TP). TP software generally determines the instantaneous leaf tip positions for an entire (static or dynamic) treatment plan based on the ideal position of both ends of each TP strip which is to receive beam. TP strips are assumed to have orthogonal ends controlled by two opposing squared-tipped MLC leaves in each strip. Besides the additional TP complexities associated with a multi-level parallel MLC, the variations of leaf tip shape do not produce orthogonal end shapes and change end shapes of TP strips as one leaf tip passes another (e.g. for two levels, a distal leaf passes a proximal leaf as shown in FIG. 13).

The disclosure provides a technique that can be used to solve the problems caused by the variations of leaf tips in treatment planning. According to the provided technique, treatment planning (TP) may simply convert the TP-desired positions assumed for overly-simplistic square leaf tips into the most-relevant averaged specific positions of various shaped leaf tips affecting each TP strip. The proposed method is to constrain the underdosed and overdosed strip area to be equal whether shaped by one leaf alone or by one leaf tip passing another. As used herein, the term "treatment strip" refers to a portion or segment of a treatment field which may be defined by a pair of opposing leaves of a single level MLC, or by two or more pairs of opposing leaves in a multi level MLC.

Therefore, the disclosure provides a method of planning a radiation treatment plan using a multi level MLC as described above. The multi level MLC comprises a first MLC in a first level comprising first beam blocking leaves longitudinally movable in a first direction and a second MLC in a second level comprising second beam blocking leaves longitudinally movable in a second direction. The first direction may be generally parallel with the second direction and the beam blocking leaves of the first MLC may laterally offset from the beam blocking leaves of the second MLC in a beam's eye view. The beam blocking leaves of the first and/or second MLCs may include an end portion having a non-square shape in a beam's eye view.

In the method, a treatment strip is determined using an imaginary leaf which comprises an end portion having a square shape in a beam's eye view. Then the position of the imaginary leaf is converted to determine the positions of the leaves of the multi-level MLC, which include a leaf end portion having a non-square shape in a beam's eye view. In determining a position for a first leaf of the first multileaf collimator and a position for a second leaf of the second multileaf collimator, the overdosed or underdose areas caused by the non-square shape of the first leaf is kept substantially equal to the underdose or overdose area caused by the non-square shape of the second leaf.

FIG. 13 schematically shows the treatment planning method described above using a two-level MLC according to some aspect of this disclosure. In FIG. 13, a proximal leaf (e.g. a leaf of a first MLC in a first level) is shown to pass through a distal leaf (e.g. a leaf of a second MLC in a second level) in defining a 5 mm TP strip. The D-X1, D-X2, D-0, P-X4, and P-X5 refer to the positions of the effective leaf tips (imaginary leaf with a leaf tip having a square shape in a beam's eye view) in the 5 mm TP strip location in the respective images. In converting to or determining the positions of the distal and proximal leaves with an end portion having a non-square shape in a beam's eye view, an overdose or underdose area in the treatment strip will be created as a result of the non-square shape of the leaf end portions. According to the technique of this disclosure, the positions of the distal leaf and proximal leaf are selected such that the underdosed and overdosed areas are kept substantially same or the dose differences are minimized.

Radiation beam penumbra occurs in systems equipped with multileaf collimators at the edges of the radiation field where the radiation intensity decreases with distance from the full intensity region of field. This phenomenon is a combination of geometric penumbra due to the radiation source size, leaf geometry, and transmission penumbra due to penetration of the radiation beam through the ends of the multileaf collimator leaves. Geometric penumbra is a function of the source size, the thickness of the leaves, the distance of the leaves from the source, and the distance of the reference plane from the source. Transmission penumbra is a function of material the leaves are made from, the thickness of the leaves and the energy of the radiation beam.

The penumbra produced by the multi level MLC of this disclosure is smaller when used in shaping various field contours. Better uniformity across large fields can be achieved. The multi level MLC of this disclosure can be used to optimize penumbra by utilizing different leaf tip design at each level and/or utilizing relative leaf end positions in each level. The multi level MLC according to embodiments of this disclosure can provide a better overall performance than single level MLCs or than MLCs with a same leaf tip configuration.

Accordingly, in some embodiments, a multi level MLC of this disclosure comprises a first MLC in a first level comprising beam blocking leaves longitudinally movable in a first direction and a second MLC in a second level comprising beam blocking leaves longitudinally movable in a second direction generally parallel with the first direction. The beam blocking leaves of the first MLC comprise a first end portion having a first shape in a beam's eye view. The beam blocking leaves of the second MLC comprise a second end portion having a second shape in a beam's eye view different from the first shape.

By way of example, the beam blocking leaves of the first MLC may comprise an end portion having a non-square shape in a beam's eye view and the beam blocking leaves of the second MLC may comprise an end portion having a square shape in a beam's eye view. The non-square shape in a beam's eye view may include a curved shape such as round or elliptic shape or a chamfer shape etc. as described above.

In some embodiments, the beam blocking leaves of the first and second MLCs may comprise end portions having different non-square shapes respectively in a beam's eye view. For example, the beam blocking leaves of both the first and second MLCs may be chamfer leaves but have different non-square shapes in a beam's eye view in terms of chamfer angles and/or dimensions of the middle portion. For another example, the beam blocking leaves of the first MLC may be chamfer leaves and the beam blocking leaves of the second MLC may be round or elliptic in a beam's eye view. Indeed, various other combinations are possible and the appended claims are not limited to the exemplary combinations described herein.

In some embodiment, alternative or in addition to the various combinations of leaf tip configurations in a beam's eye view, the beam blocking leaves of the first and second MLCs may have various combinations of leaf tip configurations in a side view. For example, the beam blocking leaves of the first MLC may have a first curved shape in a side view with a first radius, and the beam blocking leaves of the second MLC may have a second curved shape in a side view having a second radius, and the first radius may be different from the second radius.

The leaf tips of an MLC in each level may be optimized to address different needs e.g. targeting different areas. The penumbra by the combination of leaves of multiple levels may be smaller than the penumbra by leaves of each individual level alone. For example, an MLC in one level may be optimized for a center area and an MLC in another level may be optimized for an outer area. The combination of the two or more levels may achieve a better penumbra than that an individual level can achieve at the center area or the outer area respectively.

The leaf tips of an MLC in each level may be optimized for different field contours or slopes, and the combination of the multiple levels may have a better overall performance on various slopes than an individual MLC with one leaf end geometry. For example, for leaves with a leaf tip having a flat end geometry or a square shape in a beam's eye view, the best penumbra performance may occur when shaping a rectangular field (flat field contour). However, such leaves may perform less desirably on steeper slope or contour as described above. For chamfer leaves, the best penumbra performance may occur on certain slopes due to a particular chamfer angle at the leaf ends. By adopting square leaf tips in one level and chamfer leaves in another level, or by adopting different chamfer angles in different levels, a multi level MLC may achieve a better overall performance in shaping fields with different contours or slops.

A method of improving penumbra performance using a multi level MLC is therefore disclosed. The multi level MLC may comprise a first MLC in a first level comprising beam blocking leaves longitudinally movable in a first direction and a second MLC in a second level comprising beam blocking leaves longitudinally movable in a second direction. The first direction is generally parallel with the second direction and the beam blocking leaves of the first MLC laterally offset from the beam blocking leaves of the second MLC in a beam's eye view: In the method, at least a first leaf of the first MLC in the first level and at least a second leaf of the second MLC in the second level may be moved into a beam from a radiation source. The first and second leaves may overlap in a beam's eye view. The first and second leaves may be aligned with the radiation source such that the beam from the source may be tangent on both an end surface of the first leaf and an end surface of the second leaf.

Figures 14A, 14B, 14C:
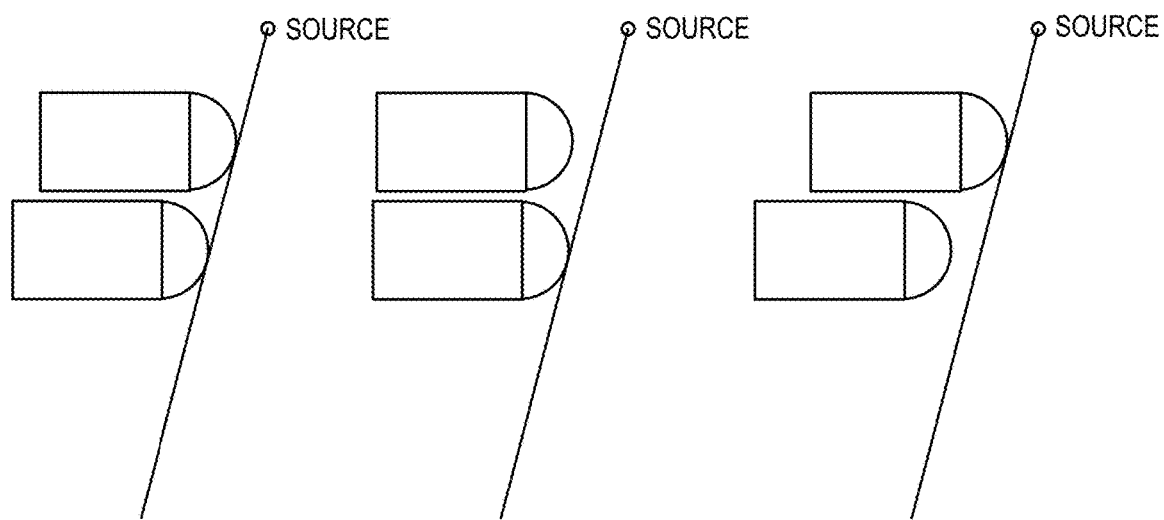
FIGS. 14A-14C schematically illustrate an exemplary method of improving penumbra performance using a multi level MLC according to some embodiments of this disclosure.

FIG. 14 schematically illustrates the method described above. It should be noted that the leaves in FIGS. 14A-14C are shown in a side view. An ideal penumbra performance or penumbra reduction may be achieved when leaves in both levels are aligned with the source because the beam transmits the most shielding materials (FIG. 14A). As such, the 100% iso-dose lines of the upper and the lower leaves may align each other at the isocenter plane. The set up in FIG. 14B is less optimal as compared to the set up in FIG. 14A. The set up in FIG. 14C may be the worst in terms of penumbra performance since the leaf end defining the field edge is closer to the source, which tends to produce greater penumbra due to the geometric projection effect of the radiation source.

A further method of shaping radiation beams using a multi level MLC is disclosed. The multi level MLC may comprise a first MLC in a first level comprising beam blocking leaves longitudinally movable in a first direction and a second MLC in a second level comprising beam blocking leaves longitudinally movable in a second direction. The first direction may be generally parallel with the second direction and the beam blocking leaves of the first MLC may laterally offset from the beam blocking leaves of the second MLC in a beam's eye view. In the method, a plurality of beam blocking leaves of the first MLC in the first level may be moved into a beam from a source, thereby the end surfaces of the plurality of the beam blocking leaves of the first MLC collectively define a first contour in a beam's eye view. The peaks of the first contour may form a first imaginary line. A corresponding plurality of beam blocking leaves of the second MLC in the second level may be moved into the beam, thereby the end surfaces of the corresponding plurality of the beam blocking leaves of the second MLC collectively define a second contour in a beam's eye view. The peaks of the second contour may form a second imaginary line. The plurality of leaves of the first MLC and the plurality of leaves the second MLC may be aligned such that the first and second imaginary lines may be substantially superimposed in a beam's eye view.

Figure 15A:
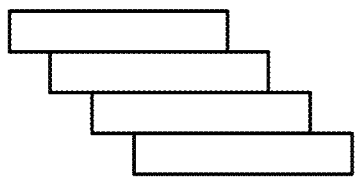
FIGS. 15A-15D schematically illustrate another exemplary method of improving penumbra performance using a multi level MLC according to some embodiments of this disclosure.
Figure 15B:
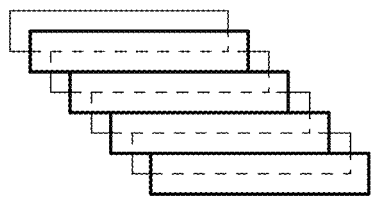
Figure 15C:
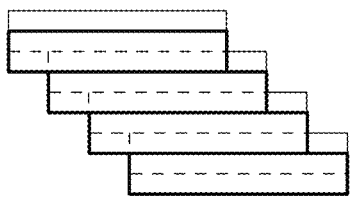
Figure 15D:
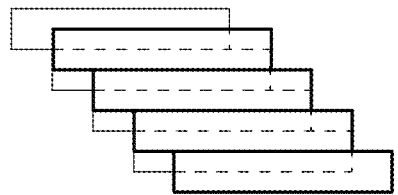

FIGS. 15A-15D schematically illustrate the method described above in shaping a field contour of 45 degree with respect to the leaf travel direction. It should be noted that the leaves shown in FIGS. 15A-15D are in a beam's eye view. FIG. 15A shows a single level MLC comprising leaves with leaf tips having a square shape in a beam's eye view. FIGS. 15B, 15C and 15D show a two-level MLC each MLC comprising leaves with leaf tips having a square shape in a beam's eye view. For a two level MLC, a desirable penumbra performance or penumbra reduction may be achieved when the peaks of the contour defined by the leaves of the first MLC and the peaks of the contour defined by the leaves of the second MLC are aligned (FIG. 15B). The set up shown in FIG. 15C is less optimal as compared to FIG. 15B. The set up in FIG. 15D may be the least desirable in penumbra performance since the upper level leaves advance in defining the field edge, which tends to produce greater penumbra due to geometric projection effects of the radiation source.

Figure 16A:
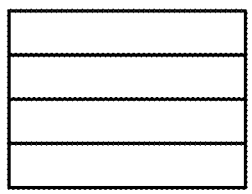
FIGS. 16A-16D schematically illustrate a further exemplary method of improving penumbra performance using a multi level MLC according to some embodiments of this disclosure.
Figure 16B:
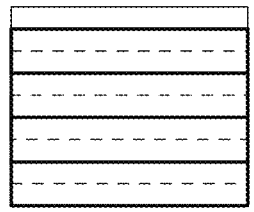
Figure 16C:
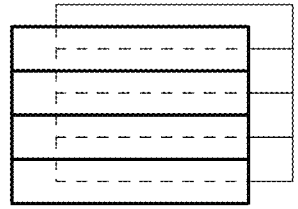
Figure 16D:
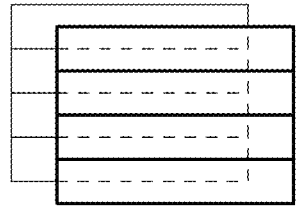

FIGS. 16A-16D schematically illustrate the method described above in shaping a vertical field contour with respect to the leaf travel direction. The leaves shown in FIGS. 16A-16D are in a beam's eye view. FIG. 16A shows a single level MLC comprising leaves with leaf tips having a square shape in a beam's eye view. FIGS. 16B, 16C and 16D show a two-level MLC each MLC comprising leaves with leaf tips having a square shape in a beam's eye view. In shaping a vertical field contour, a desirable penumbra performance or penumbra reduction may be achieved when the peaks of the contour defined by the leaves of the first MLC and the peaks of the contour defined by the leaves of the second MLC are aligned (FIG. 16 B). The set up shown in FIG. 16C is less optimal as compared to the set up of FIG. 16B. The set up shown in FIG. 16D may be the least desirable in penumbra performance as the upper level leaves advance in defining the field edge, which tends to produce greater penumbra due to geometric projection effects of the radiation source.

A further method of shaping radiation beams is disclosed according to which the penumbra performance can be optimized by utilizing the positions of MLC leaves in each of the multi levels. The multi level MLC may comprise a first MLC in a first level comprising beam blocking leaves longitudinally movable in a first direction and a second MLC in a second level comprising beam blocking leaves longitudinally movable in a second direction generally parallel with the first direction. In the method, at least a first leaf of the first MLC in the first level and at least a second leaf of the second MLC in the second level may be moved into a beam from a radiation source. The first and second leaves may overlap in a beam's eye view. The penumbra produced by the end surface of the first leaf in the isocenter plane and the penumbra produced by the end surface of the second leaf in the isocenter plane may be determined respectively. Preferably the two level leaves are aligned with the radiation source to produce the smallest penumbra as described above. In some situations where the two level leaves cannot be both aligned with the source, the leaf that produces the smaller penumbra can be advanced and aligned with the beam from the source to define the contour of the beam in the isocenter plane as the second best.

In general, the lower level MLC leaves produce smaller penumbra because they are located farther from the radiation source and closer to the isocenter plane, assuming the same source spot size and similar leaf geometry. Therefore, in general, the lower level MLC leaves may extend to the field in defining the field contour if a perfect line-up of leaves of different levels at all locations is difficult to achieve. However, there are situations where the upper level leaves may have a smaller penumbra due to the design or location of the leaves, or due to the desired field contours. In these situations, the leaves in a level whichever produce the smaller penumbra may extend to the field in shaping the field contour if a perfect line-up of leaves of all levels is difficult.

In some applications, the penumbra may be purposely increased to reduce the treatment plan complexity by adjusting the relative positions away from the best line-up position. The multi level MLC described in this disclosure may achieve more uniform and smaller penumbra than that any individual level MLC can achieve across the entire region.

FIG. 17 shows images of field edges shaped by a conventional single level MLC and two level MLCs according to embodiments of this disclosure. FIG. 17A shows an image produced by using a conventional single level MLC. FIGS. 17B and 17C show images produced by using two level MLCs according to embodiments of this disclosure. FIG. 17D shows images of a chamfer leaf and a leaf tip having a square shape in a beam's eye view. The two level MLC producing the image shown in FIG. 17B includes chamfer leaves with a leaf width about same as that of the leaves of the conventional single level MLC producing the image shown in FIG. 17A. The two level MLC producing the image shown in FIG. 17C includes square leaves with a leaf width about half of that of the chamfer leaves producing the image shown in FIG. 17B. The overall performance of the two level MLCs of this disclosure shown in FIGS. 17B and 17C is better than that of the conventional single level MLC shown in FIG. 17A, in step resolution and penumbra etc. Further, the two level MLC comprising chamfer leaves (FIG. 17B) can achieve an overall performance similar to that of the two level MLC comprising square leaves with a leaf width about half of that of the chamfer leaves. This means that a multi level MLC comprising chamfer leaves can achieve a good overall performance with a reduced manufacturing cost.

FIG. 18 shows images of effective penumbra produced by a conventional single level MLC and two level MLCs according to embodiments of this disclosure. FIG. 18A is an image showing an effective penumbra (4.7 mm) produced by using a conventional single level MLC. FIGS. 18B and 18C are images showing effective penumbra (4.3 mm and 4.0 mm respectively) produced by using two level MLCs according to embodiments this disclosure. FIG. 18 demonstrates the better penumbra performance of the multi level MLCs of this disclosure over the conventional single level MLC.

Those skilled in the art will appreciate that various other modifications may be made within the spirit and scope of the invention. All these or other variations and modifications are contemplated by the inventors and within the scope of the invention.

What is claimed is:

1. A multi level multileaf collimator comprising:
a first multileaf collimator in a first level comprising beam blocking leaves movable in a first direction; and
a second multileaf collimator in a second level comprising beam blocking leaves movable in a second direction, wherein
the first direction is generally parallel with the second direction and the leaves of the first multileaf collimator laterally offset the leaves of the second multileaf collimator;
wherein each of the beam blocking leaves of the first and second multileaf collimators comprises a top surface proximal to a radiation source when in use,
the top surface of at least some of the beam blocking leaves of the first multileaf collimator has a non-square shape viewed in a direction perpendicular to the top surface of the at least some of the beam blocking leaves of the first multileaf collimator, and
wherein the non-square shape of the top surface of the at least some of the beam blocking leaves of the first multileaf collimator comprises a middle portion orthogonal to the first direction, and a beveled portion on each side of the middle portion.

2. The multi level multileaf collimator of claim 1 wherein the top surface of the beam blocking leaves of the second multileaf collimator has a square shape viewed in a direction perpendicular to the top surface of the beam blocking leaves of the second multileaf collimator.

3. The multi level multileaf collimator of claim 1 wherein the at least some of the beam blocking leaves of the first multileaf collimator have a width, and the middle portion of non-square shape is about half of the width.

4. The multi level multileaf collimator of claim 3 wherein the beveled portion on either side of the middle portion has an angle ranging from 20-80 degrees with respect to the middle portion.

5. The multi level multileaf collimator of claim 4 wherein the beveled portion on either side of the middle portion has an angle of about 45 degree with respect to the middle portion.

6. The multi level multileaf collimator of claim 4 wherein the beveled portion on either side of the middle portion has an angle of about 60 degree with respect to the middle portion.

7. The multi level multileaf collimator of claim 1 wherein the top surface of at least some of the beam blocking leaves of the second multileaf collimator has a non-squared shape viewed in a direction perpendicular to the top surface of the at least some of the beam blocking leaves of the second multileaf collimator, wherein the non-square shape of the top surface of the at least some of the leaves of the second multileaf collimator comprise a middle portion orthogonal to the second direction and a beveled portion on each side of the middle portion.

8. The multi level multileaf collimator of claim 1 wherein the top surface of the beam blocking leaves of the second multileaf collimator has a square shape viewed in a direction perpendicular to the top surface of the at least some of the beam blocking leaves of the second multileaf collimator.

9. The multi level multileaf collimator of claim 1 wherein the top surface of the beam blocking leaves of the second multileaf collimator has a curved shape viewed in a direction perpendicular to the top surface of the at least some of the beam blocking leaves of the second multileaf collimator.

10. The multi level multileaf collimator of claim 1 wherein the top surface of the beam blocking leaves of the second multileaf collimator has a pointed angle shape viewed in a direction perpendicular to the top surface of the at least some of the beam blocking leaves of the second multileaf collimator.

11. The multi level multileaf collimator of claim 1 wherein the non-square shape of the top surface of the at least some of the beam blocking leaves of the first multileaf collimator comprises two or more beveled portions on each side of the middle portion.

12. The multi level multileaf collimator of claim 1 wherein the beam blocking leaves of the first multileaf collimator comprises a first group of leaves having a first leaf width and a second group of leaves on each side of the first group of leaves, the second group of leaves have a second leaf width thicker than the first leaf width.

13. The multi level multileaf collimator of claim 1 wherein the beam blocking leaves of the second multileaf collimator comprises a first group of leaves having a first leaf width and a second group of leaves on each side of the first group of leaves of the second multileaf collimator, the second group of leaves of the second multileaf collimator have a second leaf width thicker than the first leaf width of the second multileaf collimator.

14. The multi level multileaf collimator of claim 1 wherein the first beam blocking leaves have a curved shape in a side view with a first radius, and the second beam blocking leaves have a curved shape in a side view having a second radius, wherein the first radius is different from the second radius.

15. A multi level multileaf collimator comprising:
a first multileaf collimator in a first level comprising beam blocking leaves movable in a first direction; and
a second multileaf collimator in a second level comprising beam blocking leaves movable in a second direction, wherein
the first direction is generally parallel with the second direction and the leaves of the first multileaf collimator laterally offset the leaves of the second multileaf collimator;
wherein each of the beam blocking leaves of the first and second multileaf collimators comprises a top surface proximal to a radiation source when in use,
the top surface of at least some of the beam blocking leaves of the first multileaf collimator has a non-square shape viewed in a direction perpendicular to the top surface of the at least some of the beam blocking leaves of the first multileaf collimator, and
wherein the non-square shape of the top surface of the at least some of the beam blocking leaves of the first multileaf collimator has a curved shape, and the top surface of at least some of the beam blocking leaves of the second multileaf collimator has a curved shape viewed in a direction perpendicular to the top surface of the at least some of the beam blocking leaves of the second multileaf collimator.

* * * * *

UNITED STATES PATENT AND TRADEMARK OFFICE
CERTIFICATE OF CORRECTION

PATENT NO. : 10,722,732 B2
APPLICATION NO. : 15/844158
DATED : July 28, 2020
INVENTOR(S) : HsinLu Hsu et al.

Page 1 of 1

It is certified that error appears in the above-identified patent and that said Letters Patent is hereby corrected as shown below:

On the Title Page

Item (73) Under Assignee, please add -Varian Medical Systems International AG (CH)-.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*